United States Patent
Casanave et al.

(10) Patent No.: US 9,090,916 B2
(45) Date of Patent: Jul. 28, 2015

(54) METHOD FOR PRODUCING SWEET JUICE FROM LIGNOCELLULOSIC BIOMASS WITH IMPROVED ENZYME RECYCLE

(75) Inventors: Dominique Casanave, Saint-Genis-Laval (FR); Nicolas Lopes Ferreira, Croisilles (FR)

(73) Assignee: IFP ENERGIES NOUVELLES, Rueil-Malmaison Cedex (FR)

( * ) Notice: Subject to any disclaimer, the term of this patent is extended or adjusted under 35 U.S.C. 154(b) by 1074 days.

(21) Appl. No.: 12/809,276

(22) PCT Filed: Dec. 10, 2008

(86) PCT No.: PCT/FR2008/001719
§ 371 (c)(1), (2), (4) Date: Oct. 18, 2010

(87) PCT Pub. No.: WO2009/103878
PCT Pub. Date: Aug. 27, 2009

(65) Prior Publication Data
US 2011/0033888 A1    Feb. 10, 2011

(30) Foreign Application Priority Data
Dec. 20, 2007  (FR) ..................... 07 09121

(51) Int. Cl.
  C12P 19/02 (2006.01)
  C12P 7/10 (2006.01)
  C12P 19/14 (2006.01)

(52) U.S. Cl.
  CPC . *C12P 7/10* (2013.01); *C12P 19/02* (2013.01); *C12P 19/14* (2013.01); *Y02E 50/16* (2013.01)

(58) Field of Classification Search
  None
  See application file for complete search history.

(56) References Cited

U.S. PATENT DOCUMENTS

| | | | |
|---|---|---|---|
| 4,840,904 A * | 6/1989 | Woodward | 435/165 |
| 5,348,871 A | 9/1994 | Scott et al. | |
| 5,962,289 A | 10/1999 | Kilburn et al. | |
| 7,727,746 B2 * | 6/2010 | Foody et al. | 435/99 |

FOREIGN PATENT DOCUMENTS

| EP | 0 062 027 A2 | 10/1982 |
|---|---|---|
| JP | 2006-149343 A | 6/2006 |

OTHER PUBLICATIONS

International Search Report of PCT/FR2008/001719 (Nov. 19, 2009).
S. Xue-Liang et al., "Studies on Immobilized Cellobiase", Database Medline [Online] US National Library of Medicine (NLM) Mar. 2003, XP002498648.
X. Shen et al., "Lactic Acid Production from Cellulosic Material by Synergetic Hydrolysis and Fermentation", Applied Biochemistry and Biotechnology, vol. 133, No. 3 (Jun. 2006) pp. 251-262.
Machine Translation of the Written Opinion for the PCT application PCT/FR2008/001719, of which U.S. Appl. No. 12/809,276 is the National Stage, discussing reference (EP 0 062 027), as written in French.

* cited by examiner

*Primary Examiner* — Jon P Weber
*Assistant Examiner* — Teresa E Knight
(74) *Attorney, Agent, or Firm* — Millen, White, Zelano & Branigan, P.C.

(57) ABSTRACT

The present invention relates to a method of producing sweet juice from lignocellulosic substrate, wherein enzymatic hydrolysis is carried out by performing cellulase supplementation with supported β-glucosidases used in a reactor separate from the lignocellulose enzymatic hydrolysis reactor.

19 Claims, 5 Drawing Sheets

METHOD FOR PRODUCING SWEET JUICE FROM LIGNOCELLULOSIC BIOMASS WITH IMPROVED ENZYME RECYCLE

FIELD OF THE INVENTION

The present invention relates to the production of biofuels referred to as "second generation" biofuels. It concerns a sweet juice production method wherein enzymatic hydrolysis of lignocellulosic substrates constitutes an improvement in the use and recycle of the enzymes involved. The sweet juices thus obtained are sent to the alcoholic fermentation stage, then to the distillation stage, in order to produce an ex-biomass alcohol.

BACKGROUND OF THE INVENTION

The lignocellulosic biomass resource represents a considerable renewable energy source and it is obtained from agricultural and forest residues or from wood transformation by-products, as well as dedicated crops (woody or herbaceous plants). The lignocellulosic material consists of three major elements interlinked in a complex network. These elements are cellulose, hemicelluloses and lignin. Their respective proportions vary depending on the exact origin of the biomass.

The procedure often recommended to obtain fermentescible sugars from cellulose is enzymatic hydrolysis. Degradation of cellulose to glucose requires the synergetic action of three categories of enzymes, cellulases, classified according to their activity:

the endoglucanases cut the cellulose randomly at the level of the amorphous zones of the cellulose, the exoglucanases (or cellobiohydrolases when they produce cellobiose) act progressively on the free ends of the cellulose chains, releasing glucose or cellobiose, the β-glucosidases (or cellobiases) hydrolize the soluble cellodextrines and the cellobiose to glucose.

One of the main barriers currently limiting the industrial development of this process is the high cost associated with the production of cellulases. In order to improve the activity of commercial enzymatic cocktails, supplementation of the cellulases with β-glucosidases is described in the literature, so as to annihilate the well-known inhibiting effect of cellobiose on the activity of endo- and exoglucanases.

In order to reduce the amount of enzymes used, various solutions have been proposed to recycle these enzymes. At the end of the enzymatic hydrolysis process, the enzymes are partly in free form in the hydrolysate and partly bonded to the solid residue.

In patent FR-B-2,608,625 filed by the applicant, a method consisting in recovering the major part of the enzymes is provided: the free enzymes are recovered by adsorption on the new substrate to be converted, whereas the bonded enzymes are used again by recontacting the solid residue with the new substrate. In cases where the cellulases are supplemented with β-glucosidases to improve the activity of the enzymatic cocktail, the method provided is however not satisfactory: after recycling, a significant activity loss is observed, associated with the accumulation of cellobiose (Ramos et al, *Applied Biochemistry and Biotechnology*, 1994, 45 (6), 193-207). In fact, this method does not allow to efficiently recycle the free β-glucosidases that have very little affinity with the lignocellulosic substrate.

Supplementation of commercial cellulases with supported β-glucosidases is a method described by Woodward et al. ("Use of immobilized beta-glucosidase in the hydrolysis of cellulose", 1993, *ACS symposium series*, 533, 240-250) which allows to re-use several times the β-glucosidases without any activity loss or appreciable decrease in the conversion of cellulose to glucose. Immobilization of the β-glucosidases allows their stability to be notably improved: Aguado et al. (*Biotechnology and Applied Biochemistry*, 1995, 17(1), 49-55) showed that the immobilization of *Penicillium funiculosum* β-glucosidases on nylon powder allows to obtain a stable activity for 1500 min at 50° C., whereas the same enzymes in the free state deactivate from 40° C. on. *Aspergillus niger* β-glucosidases are stable in the free state up to 45° C., whereas in immobilized form on Eupergit C, their activity remains stable up to 65° C. (Tu et al, 2006, *Biotechnology Letters*, 28 (3), 151-156). On the other hand, at such temperatures, the cellulases show little stability and they rapidly deactivate, which impacts the hydrolysis efficiency.

Recycling the supported β-glucosidases requires extracting them from the reaction mixture containing a solid residue, which cannot be readily done when the cellulases and the β-glucosidases are used in the same reactor.

On the other hand, non-productive adsorption of the β-glucosidases on lignin is a known source of limitation of enzymatic hydrolysis. One known solution for limiting this adsorption consists in adding surfactants and/or proteins such as bovine serum albumin (BSA) (Yang et al., 2006, Biotechnology and Bioengineering, 94 (4), 611-617).

These main limitations can be raised by implementing the sweet juice production method according to the present invention.

SUMMARY OF THE INVENTION

The method according to the present invention consists in producing sweet juices through enzymatic hydrolysis of lignocellulosic substrates by performing supplementation of the cellulases with supported β-glucosidases, used in a reactor separate from the lignocellulose enzymatic hydrolysis reactor, hydrolysate H1 obtained at the outlet of reactor (1) being sent to a separation means allowing to extract the cellulases prior to being sent to reactor (2).

The present invention also describes the device in which the enzymatic hydrolysis method is carried out.

DETAILED DESCRIPTION

The present invention relates to a method of producing sweet juice from lignocellulosic substrate by enzymatic hydrolysis, wherein cellulase supplementation is carried out with supported β-glucosidases, in a reactor (2) separate from lignocellulose enzymatic hydrolysis reactor (1), wherein said substrate, which has been pretreated beforehand, is contacted with a cellulase solution, hydrolysate H1 obtained at the outlet of reactor (1) being sent to a separation means allowing to extract the cellulases prior to being sent to reactor (2), said method comprising a lignocellulose conversion stage, a sweet juice production stage and a stage of complete emptying of the reactors.

The method according to the invention notably allows to improve enzyme recycle by facilitating extraction of the β-glucosidases from the reaction medium.

Another advantage of the method according to the present invention is to be able to dissociate the operating conditions (temperature and possibly pH value) of the two reactors and consequently to optimize them in the second reactor peculiar to the β-glucosidases. The cellulases are extracted at the outlet of reactor (1) and they are not sent to the second reactor.

Furthermore, in the method according to the present invention, the supported β-glucosidases are not in contact with the lignin that remains in the reactor dedicated to lignocellulose enzymatic hydrolysis.

The method according to the present invention allows to produce a glucose-rich sweet juice from lignocellulosic substrates.

The substrates used are selected from among straws, wood, forest crops, alcohol-producing crop, sugar crop and cereal crop residues, paper industry residues, cellulosic and lignocellulosic material transformation products.

In the process according to the present invention, hydrolysate (H1) obtained at the outlet of reactor (1) is sent to an ultrafiltration membrane (7) allowing to extract the cellulases The sweet juice production method according to the present invention comprises a lignocellulose conversion stage, a sweet juice production stage proper and a stage of complete emptying of the reactors.

To implement the method according to the present invention, a lignocellulosic substrate (S), pretreated beforehand, is contacted in reactor (1) with a cellulase solution (E) under dilution, temperature and pH conditions favourable to the enzymatic hydrolysis of lignocellulose. The pretreatment performed according to techniques known to the person skilled in the art allows to improve the susceptibility of the substrate to enzymatic hydrolysis.

Figure 1:
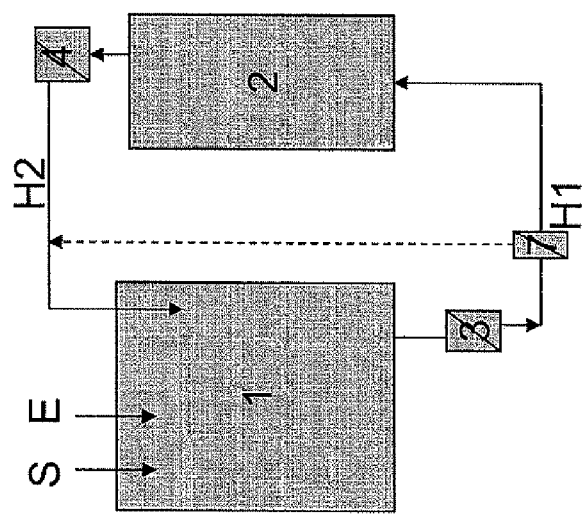
FIG. 1 is a flow diagram of the method according to the present invention corresponding to the lignocellulose conversion stage.

When the substrate starts to liquefy (FIG. 1), the lignocellulose conversion stage produces a hydrolysate continuously extracted from reactor (1) into a filter medium (3) and a separation means (7) so that the solid fraction (enzymatic hydrolysis solid residue) and the cellulases present in the reaction mixture remain in reactor (1). After passage through filter medium (3) and separation means (7), hydrolysate (H1) containing non-fermentescible soluble glucose oligomers is injected into reactor (2) where it is contacted with supported β-glucosidases, under temperature conditions favourable to the hydrolysis of soluble glucose oligomers (cellobiose, cellotriose . . . ) to glucose. The residence time of sweet juice (H1) in reactor (2) is adjusted in such a way that the proportion of residual soluble oligomers is very low (preferably below 1 g/l) in the hydrolysate obtained at the outlet of reactor (2).

The temperature in reactor (1) preferably ranges between 40° C. and 55° C., the temperature in reactor (2) between 40° C. and 70° C.

The temperature and/or pH operating conditions of reactors (1) and (2) can be different or identical.

The operating conditions in reactors (1) and (2) are preferably different. More preferably, the temperature in reactor (1) ranges between 45° C. and 55° C., and the temperature in reactor (2) ranges between 60° C. and 70° C.

Separation means (7) preferably is an ultrafiltration membrane. At the outlet of this membrane, the cellulase-freed permeate is sent to reactor (2), whereas the retentate is mixed with stream (H2) leaving reactor (2). This embodiment notably allows to operate reactor (2) for example at higher temperatures than those commonly used for cellulases.

The hydrolysate poor in soluble oligomers (H2) is continuously extracted from reactor (2) into a filter medium (4) in such a way that the supported β-glucosidases present in the reaction mixture remain in reactor (2): filter medium (4) is selected according to the grain size of the support selected for immobilizing the supported enzymes.

During the conversion stage, the major part of stream (H2) and preferably all of the stream (H2) produced is reinjected into reactor (1).

Figure 2:
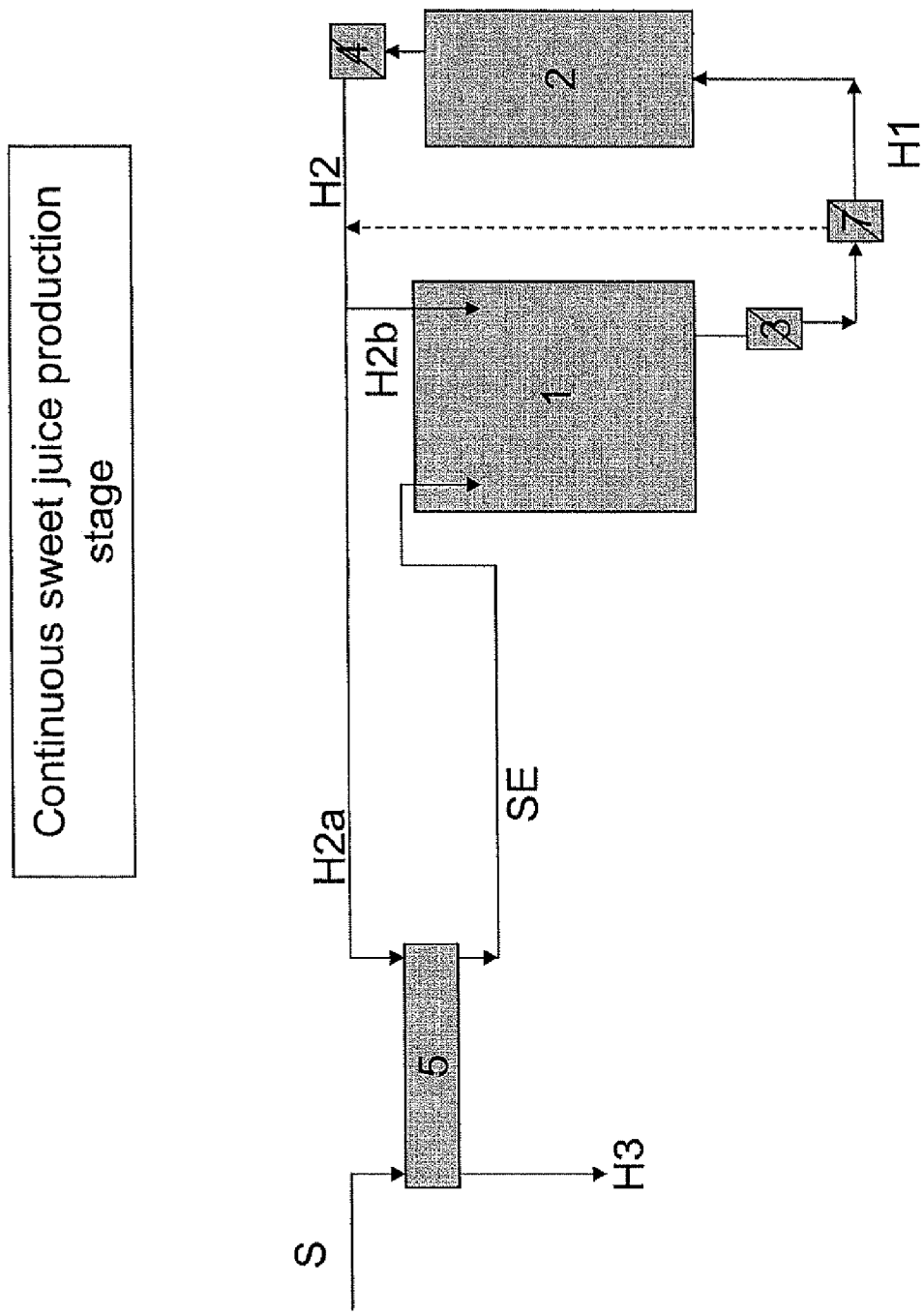
FIG. 2 is a flow diagram of the method according to the present invention corresponding to the continuous sweet juice production stage, FIG. 3 correspond to the flow diagrams of the sweet juice production method according to the invention implemented in batch mode, FIG. 3A corresponding to the stage of emptying the two reactors and FIG. 3B to the stage of filling the reactors.
Figure 3A:
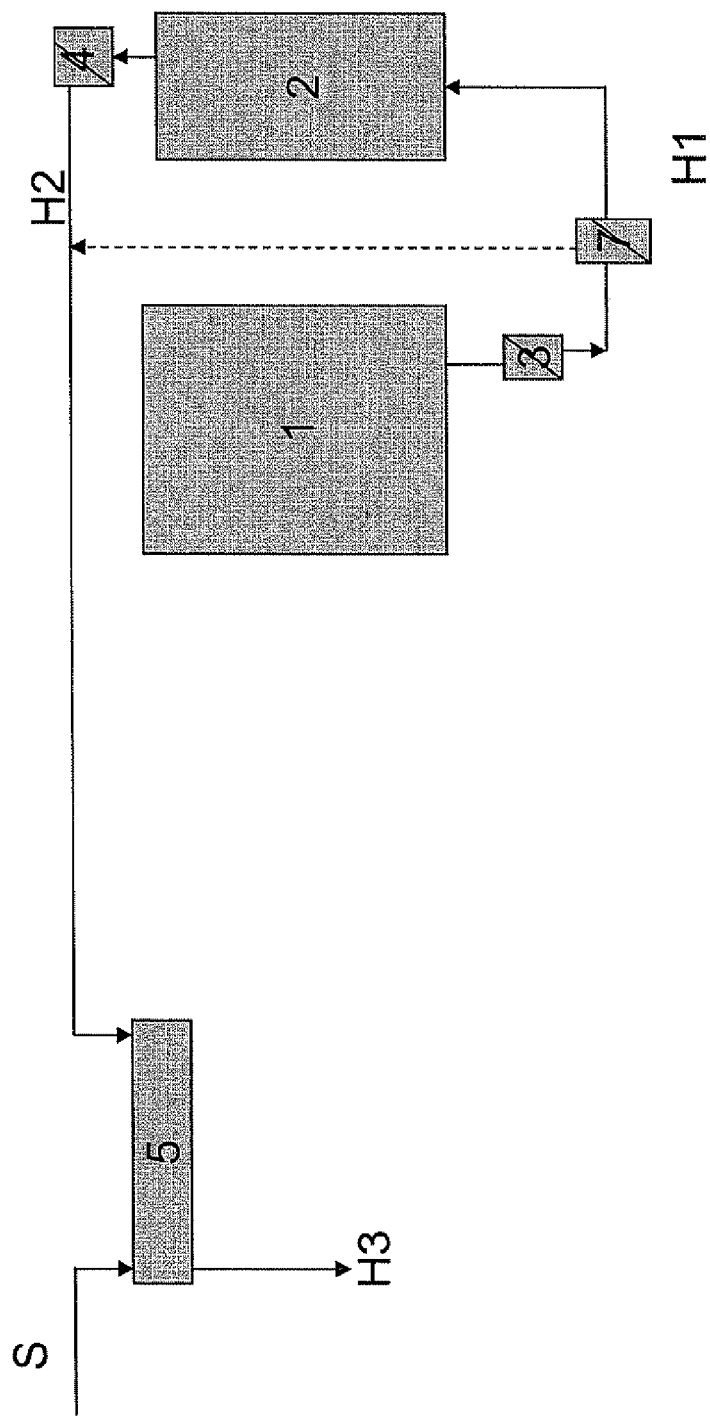
Figure 3B:
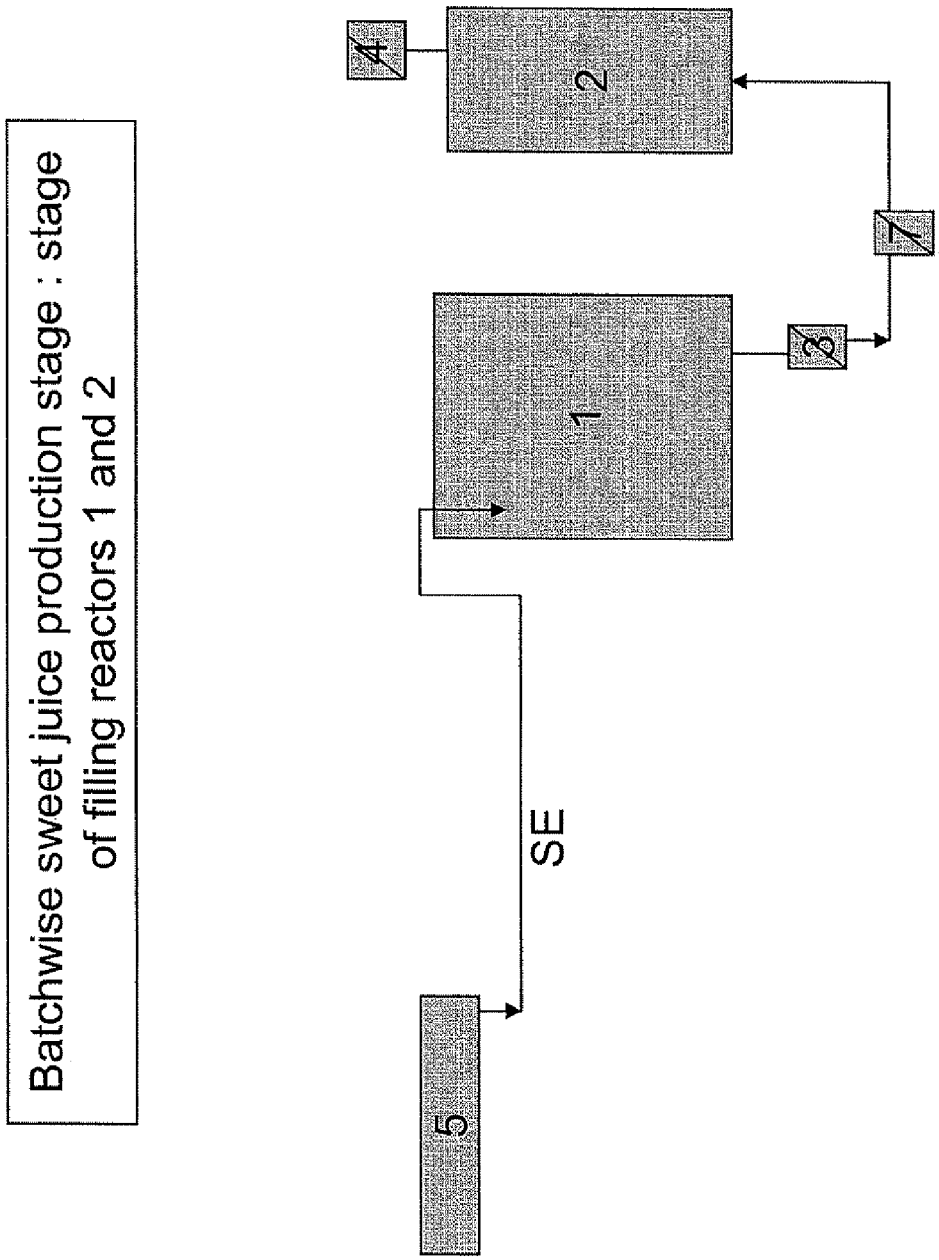

When conversion is considered sufficient, i.e. when the measurement performed shows that the desired sugar concentration in hydrolysate (H2) is reached, the sweet juice production stage proper, illustrated by FIGS. 2 and 3, is started.

The sweet juice production stage can be carried out according to two modes: continuous mode or batch mode.

According to the first embodiment, the production stage is carried out in continuous mode. The hydrolysate stream (H2) from reactor (2) is separated into at least two streams (H2a) and (H2b).

Stream (H2a) is continuously fed into a contactor (5). This hydrolysate (H2a) is contacted in equipment (5) with new lignocellulosic substrate (S) so that the cellulases present in hydrolysate (H2a) adsorb on the new substrate.

Stream (H2b), poor in soluble oligomers, is reinjected into reactor (1), thus allowing to improve the mixing conditions in the reactor and to promote the cellulase activity through the induced diluting effect, soluble oligomers being in fact known as cellulase activity inhibiting products.

The cellulase-impregnated new substrate (SE) from contactor (5) is separated from hydrolysate (H3) prior to being sent to reactor (1).

Hydrolysate (H3) collected at the outlet of contactor (5) corresponds to the sweet juice stream produced by the method.

According to the second embodiment of the method according to the invention, the production stage is carried out in batch mode and in two steps (FIGS. 3A and 3B), the first step consisting in emptying the reactors, the second in starting them up again.

The reactors are first emptied: stream (H2) from reactor (2) is sent to contactor (5) where it is contacted with new lignocellulosic substrate (S) so that the cellulases fed into hydrolysate (H2) at the outlet of separation means (7) adsorb on the new substrate. Hydrolysate (H3) obtained at the contactor outlet corresponds to the sweet juice stream produced by the method.

At the end of the reactor emptying stage, the production stage is started again in batch mode (FIG. 3B), by feeding the cellulase-impregnated new substrate into reactor (1).

Figure 4:
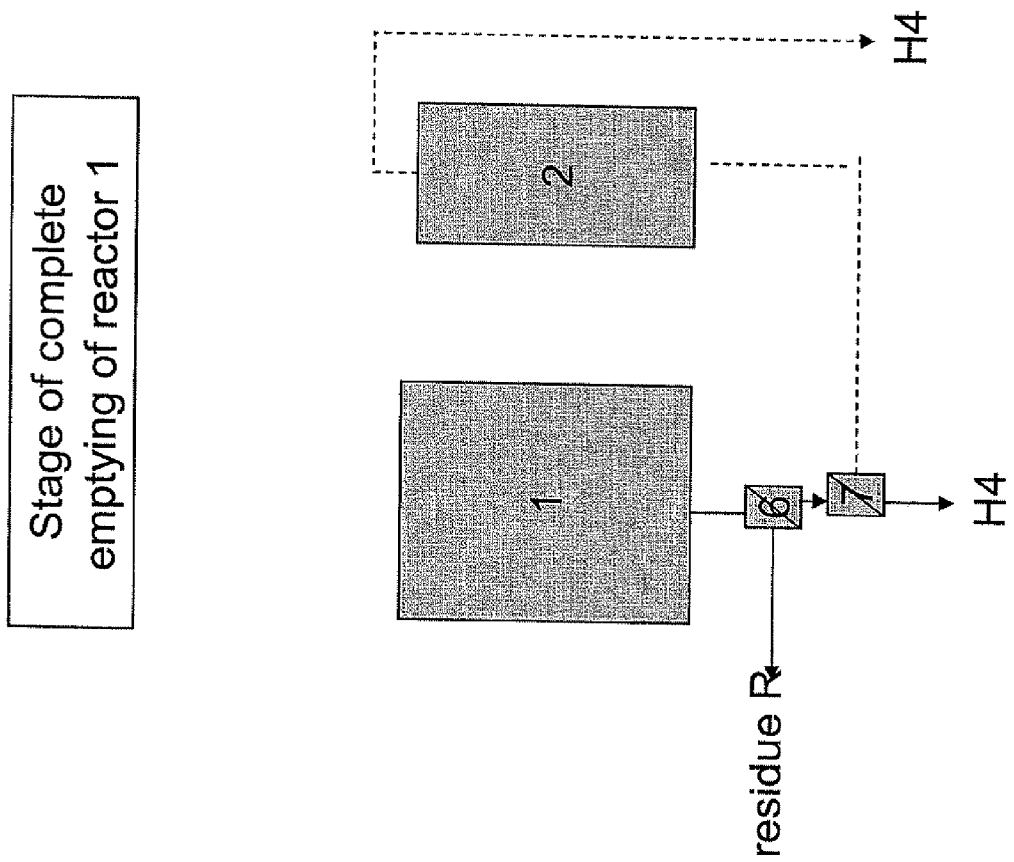
FIG. 4 is a flow diagram of the method according to the present invention corresponding to the stage of complete emptying of the lignocellulose enzymatic hydrolysis reactor.

When the amount of solid residue accumulated in reactor (1) becomes too great, this reactor is completely emptied (FIG. 4). The reaction mixture recovered is sent to a filter medium (6) so as to separate the solid fraction (residue R) corresponding to the enzymatic hydrolysis residue, then to separation means (7) at the outlet of which a liquid fraction (H4) is obtained.

This liquid fraction (H4) is a sweet juice. In order to optimize the glucose production, if this fraction (H4) contains residual soluble oligomers, it is possible to send it to reactor (2) prior to extracting it.

Fraction (H4) corresponding to the stream produced by the method during the emptying stage can possibly be partly or totally reintroduced into reactor (1) during the enzymatic hydrolysis starting phase, by reintroducing fresh cellulases and new substrate, or it can be used for impregnating new substrate in contactor (5).

The present invention also describes the device wherein the sweet juice production method described above is implemented.

Said device intended for sweet juice production by enzymatic hydrolysis from lignocellulosic substrate comprises:

at least a first lignocellulose enzymatic hydrolysis reactor (1), said reactor (1) being provided with at least one line for introducing the substrate and the cellulase solution, at least one line for withdrawing the converted juice (H1) and sending it to at least one filter medium (3) arranged at the outlet of reactor (1), and at least one separation means (7), that is preferably an ultrafiltration membrane, for extracting the cellulases from the hydrolysate, possibly a heat exchanger at the outlet of the first reactor (not shown in the figures), at least a second reactor (2) comprising the supported β-glucosidases, connected to said separation means (7) by at least one line, said reactor (2) being equipped at the outlet thereof with at least one filter medium (4) and at least one line for extracting stream (H2) consisting of the hydrolysate poor in soluble oligomers, at least one line for feeding at least part of stream (H2) into a contactor (5) and at least one line for sending back at least part of stream (H2) to reactor (1), at least one contactor (5) provided with at least one line for introducing the new substrate, at least one line for extracting the sweet juice produced (H3) and at least one line for discharging the cellulase-impregnated new substrate and feeding it into reactor (1).

Said device comprises at least one filter medium (6) used during the stage of complete emptying of reactor (1), at least one line for extracting solid residue R, at least one line for extracting the sweet juice stream (H4) produced and possibly at least one line for feeding stream (H4) into reactor (2).

Reactor (1) can be a mechanically stirred tank or not. Stirring can also be entirely or partly provided by the sweet juice circulation loop around reactor (1) (stream H2$b$ or stream H2), using high injection rates.

Filter media (3) and (6) allowing to extract the liquid fraction from the reaction mixture are suited to the grain size of the solid lignocellulosic substrate. Any equipment known to the person skilled in the art can be used to achieve this fractionation: filtering system installed inside or outside the reactor, including the associated backwashing or cleaning system (filtering candles, mechanically scraped grate, . . . ), external separation module with reinjection of the solid fraction into the reactor (filter press, centrifuge, . . . ). Dimensioning of these equipments has to be suited to the volume to be processed.

These filter media (3), (6) and separation means (7) can possibly be one and the same.

Implementation of the enzymes immobilized in reactor (2) can be carried out in a fixed bed or in a moving bed, or in a stirred slurry type reactor. The purpose of filter medium (4) is to maintain the supported enzymes in reactor (2).

In the case of a fixed bed, which is the preferred embodiment, this medium (4) can be a grate or a guard bed arranged in the reactor.

For the other embodiments (moving bed or stirred slurry type reactor), the equipments described above for filter medium (3) can also be suitable for filter medium (4).

In order to compensate for the deactivation of the supported β-glucosidases, continuous fresh enzyme makeup combined with deactivated enzyme withdrawal can be carried out when using moving or slurry beds. In the case of a fixed bed, replacement of the deactivated enzymes by new enzymes is done in batch mode during the stage of emptying reactors (1) and (2) for example.

The cellulose recycle carried out in equipment (5) can be performed by contacting hydrolysate (H2$a$) or (H4) with pretreated fresh lignocellulosic substrate, said contact occurring for example by percolation or resuspension and separation, so as to recover the cellulases by adsorption, according to any method known to the person skilled in the art. Equipment (5) can thus be an equipment similar to the one described for the assembly made up of reactor (1) and filter medium (3), wherein substrate resuspension and filtration can be carried out.

Equipment (5) can also be any technology type allowing to achieve liquid-solid contacting by percolation of the liquid on the solid in batch mode, or preferably in continuous mode. In the case of percolation contact, equipment (5) can also include a filter press system allowing to reduce the amount of sweet juice reintroduced into reactor (1).

Preparation of the supported or immobilized β-glucosidases is carried out from β-glucosidases produced by strains of fungi belonging to the *Trichoderma, Aspergillus, Penicillium* or *Schizophyllum* genera, for example by *Aspergillus niger, Penicillium funiculosum* or *Trichoderma reesei*. These strains may have been genetically modified. Their immobilization is performed using any type of support (solid or gel) known to the person skilled in the art (resins, Eupergit C, activated carbon nanotubes, alumina coated with a polymer matrix, activated nylon powder, calcium alginate, chitosan, . . . ).

The following examples illustrate the present invention without limiting the scope thereof.

Example 1

Wheat Straw Enzymatic Hydrolysis with Enzyme Recycle, According to the Teachings of patent FR-B-2,608,625 (Non-Supported β-Glucosidases)

A wheat straw sample was pretreated by steam explosion in the presence of sulfuric acid so as to improve its digestibility, i.e. its reactivity to enzymatic hydrolysis. The composition of this pretreated and washed sample is as follows: 56.5% cellulose, 14.6% hemicellulose, 25.6% lignin and extractible compounds (in % dry matter). Enzymatic hydrolysis of this sample was carried out in the presence of commercial cellulases marketed by SAF-ISIS (reference XL-E508) complemented with β-glucosidases marketed by Novozyme (reference SP-188). The amount of cellulases used in the tests is expressed in international filter paper units (FPU), the amount of β-glucosidases in international units (IU) (1 IU=1 μmol glucose produced per min from cellobiose).

A first series of tests (A1, B1, C1 corresponding respectively to tests A, B and C carried out under conditions 1) was carried out in 3 stirred reactors containing each 100 g substrate (expressed in dry matter), 480 FPU (cellulases), 1000 IU (β-glucosidases) in a final volume of 1 liter. The pH value was adjusted to 4.8 and the temperature to 50° C. After 72 hours hydrolysis, the solid residues were separated by centrifugation and the sugars formed in the hydrolysate were subjected to determination by high-performance liquid chromatography (HPLC). A second series of tests (A2, B2, C2) was carried out under the same conditions as in the first series of tests, except for the following points:

test B2 was carried out without fresh enzyme addition, but the soluble enzymes were recycled by recontacting the hydrolysate obtained at the end of test B1 with the new substrate, and 100% of the solid residue obtained at the end of test B1 was recycled, test C2 was carried out identically to test B2, by adding 1000 IU of fresh β-glucosidases.

A third and last series of tests (A3, B3, C3) was carried out under conditions strictly identical to those of the second series of tests.

The results obtained are shown in Table 1. The sugars produced after each series of tests are measured from the determination of the sugars present in the final hydrolysate. For series B and C, quantification of the sugars produced during the $2^{nd}$ and $3^{rd}$ series of tests is performed by counting the sugars present when starting the enzymatic hydrolysis (sugars contained in the solid residue).

Example 2

Wheat Straw Enzymatic Hydrolysis with Enzyme Recycle and Use of Supported β-Glucosidases in a Separate Reactor According to the Method Described in the Present Invention A series of hydrolysis tests was carried out with the same wheat straw as in Example 1.

A first hydrolysis operation D1 was carried out in a stirred reactor containing 100 g substrate (expressed in dry matter) and 480 FPU (cellulases) in a final volume of 1 liter. The pH value was adjusted to 4.8 and the temperature to 50° C. After 6 hours hydrolysis, the liquid fraction of the reaction mixture was continuously extracted through a filter medium, of ultrafiltration membrane type, at a flow rate of 10 ml/min so as to continuously feed the hydrolysate without cellulases by means of a pump into a second reactor filled with a fixed bed of β-glucosidases supported on Eupergit C, prepared according to the protocol described by Tu et al., and containing 1000 IU (β-glucosidases activity). The temperature of the second reactor was maintained at 60° C. The whole of the stream leaving this second reactor was reinjected into the first enzymatic hydrolysis reactor. After 66 hours operation, the two reactors were emptied. The solid residue was separated by centrifugation and the sugars formed in the hydrolysate were subjected to determination by HPLC.

TABLE 1

Wheat straw enzymatic hydrolysis with or without enzyme recycle

| | | | Reference case without enzyme recycle Test A | Enzyme recycle without beta-glucosidase complementation Test B | Enzyme recycle with beta-glucosidase complementation Test C |
|---|---|---|---|---|---|
| Operation 1 | Conditions | Wheat straw substrate (g) | 100 | 100 | 100 |
| | | Fresh cellulases (FPU) | 480 | 480 | 480 |
| | | Fresh beta-glucosidases (IU) | 1000 | 1000 | 1000 |
| | | Enzyme recycle | none | none | none |
| | Sugars produced | Cellobiose (g) | 0 | 0 | 0 |
| | | Glucose (g) | 42.9 | 42.9 | 42.9 |
| Operation 2 | Conditions | Wheat straw substrate (g) | 100 | 100 | 100 |
| | | Fresh cellulases (FPU) | 480 | 0 | 0 |
| | | Fresh beta-glucosidases (IU) | 1000 | 0 | 1000 |
| | | Enzyme recycle | none | 100% | 100% |
| | Sugars produced | Cellobiose (g) | 0 | 5.2 | 0 |
| | | Glucose (g) | 42.9 | 17.3 | 30.5 |
| Operation 3 | Conditions | Wheat straw substrate (g) | 100 | 100 | 100 |
| | | Fresh cellulases (FPU) | 480 | 0 | 0 |
| | | Fresh beta-glucosidases (IU) | 1000 | 0 | 1000 |
| | | Enzyme recycle | none | 100% | 100% |
| | Sugars produced | Cellobiose (g) | 0 | 7.3 | 0 |
| | | Glucose (g) | 42.9 | 14.5 | 25.7 |
| overall balance | Conditions | Wheat straw substrate (g) | 300 | 300 | 300 |
| | | Fresh cellulases (FPU) | 1440 | 480 | 480 |
| | | Fresh beta-glucosidases (IU) | 3000 | 1000 | 3000 |
| | Total glucose produced | | 128.7 | 74.7 | 99.059 |
| | % glucose produced/reference case | | 100 | 58.0 | 77.0 |
| | Glucose produced per unit of enzymes (mg/FPU) | | 89.4 | 155.6 | 206.4 |

The results of the series of tests B, corresponding to the method described in patent FR-B-2,608,625, show that the performances obtained during operations 2 and 3 are markedly degraded: the production of glucose at the end of the 3 hydrolysis operations represents only 58% of the reference case. Addition of new β-glucosidases during operations 2 and 3, for the series of tests C, allows the performances to be improved: the production of glucose at the end of the 3 hydrolysis operations represents 77% of the reference case (test A).

A second operation D2 was carried out under the same conditions as in D1, except for the following points:

test D2 was carried out without fresh enzyme addition, but the soluble enzymes were recycled by recontacting the hydrolysate obtained at the end of test D1 with the new substrate, and 100% of the solid residue obtained at the end of test D1 was recycled.

A third operation D3 was carried out under conditions strictly identical to those of test D2.

The results obtained are shown in Table 2.

TABLE 2

Wheat straw enzymatic hydrolysis according to the invention

|  |  |  | Reference case without enzyme recycle Test A | According to invention Test D |
|---|---|---|---|---|
| Operation 1 | Conditions | Wheat straw substrate (g) | 100 | 100 |
|  |  | Fresh cellulases (FPU) | 480 | 480 |
|  |  | Fresh beta-glucosidases (IU) | 1000 | 1000 |
|  |  | Enzyme recycle |  | none |
|  | Sugars produced | Cellobiose (g) | 0 | 0 |
|  |  | Glucose (g) | 42.9 | 48.2 |
| Operation 2 | Conditions | Wheat straw substrate (g) | 100 | 100 |
|  |  | Fresh cellulases (FPU) | 480 | 0 |
|  |  | Fresh beta-glucosidases (IU) | 1000 | 0 |
|  |  | Enzyme recycle | none | 100% |
|  | Sugars produced | Cellobiose (g) | 0 | 0 |
|  |  | Glucose (g) | 42.9 | 35.2 |
| Operation 3 | Conditions | Wheat straw substrate (g) | 100 | 100 |
|  |  | Fresh cellulases (FPU) | 480 | 0 |
|  |  | Fresh beta-glucosidases (IU) | 1000 | 0 |
|  |  | Enzyme recycle | none | 100% |
|  | Sugars produced | Cellobiose (g) | 0 | 0 |
|  |  | Glucose (g) | 42.9 | 29.9 |
| Overall balance | Conditions | Wheat straw substrate (g) | 300 | 300 |
|  |  | Fresh cellulases (FPU) | 1440 | 480 |
|  |  | Fresh beta-glucosidases (IU) | 3000 | 1000 |
|  | Total glucose produced |  | 128.7 | 113.27 |
|  | % glucose produced/reference case |  | 100 | 88.0 |
|  | Glucose produced per unit of enzyme (mg/FPU) |  | 89.4 | 236.0 |

The use of supported β-glucosidases in a separate reactor allows the performances to be markedly improved: the production of glucose at the end of the 3 hydrolysis operations represents 88% of the reference case (test A).

Example 3

Wood Pulp Enzymatic Hydrolysis with Enzyme Recycle, According to the Teachings of patent FR-B-2,608,625 (Non-Supported β-Glucosidases)

The series of tests described in Example 1 were repeated with a non-bleached wood pulp sample. The composition of this sample was as follows: 70.3% cellulose, 15.9% hemicellulose, 7.6% lignin and extractible compounds (in % dry matter). The results obtained after 48 hours hydrolysis are shown in Table 3.

TABLE 3

Wood pulp enzymatic hydrolysis with or without enzyme recycle

|  |  |  | Reference case without enzyme recycle Test A | Enzyme recycle without beta-glucosidase complementation Test B | Enzyme recycle with beta-glucosidase complementation Test C |
|---|---|---|---|---|---|
| Operation 1 | Conditions | Wood pulp substrate (g) | 100 | 100 | 100 |
|  |  | Fresh cellulases (FPU) | 1400 | 1400 | 1400 |
|  |  | Fresh beta-glucosidases (IU) | 5000 | 5000 | 5000 |
|  |  | Enzyme recycle | none | none | none |
|  | Sugars produced | Cellobiose (g) | 0 | 0 | 0 |
|  |  | Glucose (g) | 75 | 75 | 75 |
| Operation 2 | Conditions | Wood pulp substrate (g) | 100 | 100 | 100 |
|  |  | Fresh cellulases (FPU) | 1400 | 0 | 0 |
|  |  | Fresh beta-glucosidases (IU) | 5000 | 0 | 5000 |
|  |  | Enzyme recycle | none | 100% | 100% |
|  | Sugars produced | Cellobiose (g) | 0 | 4.9 | 0 |
|  |  | Glucose (g) | 75 | 47.9 | 54.1 |
| Operation 3 | Conditions | Wood pulp substrate (g) | 100 | 100 | 100 |
|  |  | Fresh cellulases (FPU) | 1400 | 0 | 0 |
|  |  | Fresh beta-glucosidases (IU) | 5000 | 0 | 5000 |
|  |  | Enzyme recycle | none | 100% | 100% |

TABLE 3-continued

Wood pulp enzymatic hydrolysis with or without enzyme recycle

|  |  |  | Reference case without enzyme recycle Test A | Enzyme recycle without beta-glucosidase complementation Test B | Enzyme recycle with beta-glucosidase complementation Test C |
|---|---|---|---|---|---|
| overall balance | Sugars produced | Cellobiose (g) | 0 | 7.3 | 0 |
|  |  | Glucose (g) | 75 | 34.9 | 44.9 |
|  | Conditions | Wood pulp substrate (g) | 300 | 300 | 300 |
|  |  | Fresh cellulases (FPU) | 4200 | 1400 | 1400 |
|  |  | Fresh beta-glucosidases (IU) | 15000 | 5000 | 15000 |
|  | Total glucose produced |  | 225 | 157.8 | 174 |
|  | % glucose produced/reference case |  | 100.0 | 70.1 | 77.3 |
|  | Glucose produced per unit of enzymes (mg/FPU) |  | 53.6 | 112.7 | 124.3 |

The results of the series of tests B, corresponding to the method described in patent FR-B-2,608,625, show that the performances obtained during operations 2 and 3 are markedly degraded: the production of glucose at the end of the 3 hydrolysis operations represents only 70.1% of the reference case. Addition of new β-glucosidases during operations 2 and 3 for the series of tests C allows the performances to be improved: the production of glucose at the end of the 3 hydrolysis operations represents 77.3% of the reference case (test A).

Example 4

Wood Pulp Enzymatic Hydrolysis with Enzyme Recycle and Use of Supported β-Glucosidases in a Separate Reactor According to the Method Described in the Present Invention A series of enzymatic hydrolysis tests was carried out with the same wood pulp as in example 3 and under implementation conditions strictly identical to those described in Example 2, with a hydrolysis time limited to 48 hours and enzyme proportions adjusted for the new substrate selected (1400 FPU cellulases and 5000 IU immobilized β-glucosidases).

TABLE 4

Wood pulp enzymatic hydrolysis according to the invention

|  |  |  | Reference case without enzyme recycle Test A | According to Invention Test D |
|---|---|---|---|---|
| Operation 1 | Conditions | Wood pulp substrate (g) | 100 | 100 |
|  |  | Fresh cellulases (FPU) | 1400 | 1400 |
|  |  | Fresh beta-glucosidases (IU) | 5000 | 5000 |
|  |  | Enzyme recycle | none | none |
|  | Sugars produced | Cellobiose (g) | 0 | 0 |
|  |  | Glucose (g) | 75 | 75 |
| Operation 2 | Conditions | Wood pulp substrate (g) | 100 | 100 |
|  |  | Fresh cellulases (FPU) | 1400 | 0 |
|  |  | Fresh beta-glucosidases (IU) | 5000 | 0 |
|  |  | Enzyme recycle | none | 100% |
|  | Sugars produced | Cellobiose (g) | 0 | 0 |
|  |  | Glucose (g) | 75 | 68.9 |
| Operation 3 | Conditions | Wood pulp substrate (g) | 100 | 100 |
|  |  | Fresh cellulases (FPU) | 1400 | 0 |
|  |  | Fresh beta-glucosidases (IU) | 5000 | 0 |
|  |  | Enzyme recycle | none | 100% |
|  | Sugars produced | Cellobiose (g) | 0 | 0 |
|  |  | Glucose (g) | 75 | 64.2 |
| Overall balance | Conditions | Wood pulp substrate (g) | 300 | 300 |
|  |  | Fresh cellulases (FPU) | 4200 | 1400 |
|  |  | Fresh beta-glucosidases (IU) | 15000 | 5000 |
|  | Total glucose produced |  | 225 | 208.1 |
|  | % glucose produced/reference case |  | 100.0 | 92.5 |
|  | Glucose produced per unit of enzyme (mg/FPU) |  | 53.6 | 148.6 |

The use of supported β-glucosidases in a separate reactor again allows to markedly improve the performances: the production of glucose at the end of the 3 hydrolysis operations represents 92.5% of the reference case (test A).

The invention claimed is:

1. A method of producing a lignocellulosic hydrolyzate (sweet juice) for alcoholic fermentation from a lignocellulosic substrate by enzymatic hydrolysis, comprising
   (a) a lignocellulose conversion stage, comprising
   (1) contacting the lignocellulosic substrate with a cellulase solution in a first reactor to produce a first hydrolyzate, wherein said lignocellosic substrate has been pretreated to improve the susceptibility of the substrate to enzymatic hydrolysis;
   (2) sending the thus-produced first hydrolyzate obtained at the outlet of said first reactor to a separation means, whereby cellulases in the first hydrolyzate are extracted from the first hydrolyzate and retained by the separation means for return to the first reactor, to produce a cellulase-free first hydrolyzate;
(3) sending the cellulase-free first hydrolyzate to a second reactor comprising immobilized β-glucosidases, wherein said second reactor is separate from said first lignocellulose enzymatic hydrolysis reactor, to produce a second hydrolyzate, and separating the second hydrolyzate from the immobilized β-glucosidases;
(b) a sweet juice production stage, comprising
(1) adding the retained cellulases from the separation means in step (a)(2) to the second hydrolyzate;
(2) contacting said second hydrolyzate including retained cellulases with new lignocellulosic substrate, whereby retained cellulases in the second hydrolyzate are adsorbed by the new substrate and a third hydrolyzate (first sweet juice) for alcoholic fermentation is produced, and
(3) recycling the cellulases adsorbed to the new substrate to said first reactor; and
(c) a reactor emptying stage, comprising completely emptying the first and second reactors.

2. The method of claim 1, wherein the sweet juice production stage is carried out in batch mode, comprising
(i) completely emptying the first and second reactors, during which the retained cellulases from the separation means in step (a)(2) are added to said second hydrolyzate from said second reactor, the second hydrolysate including retained cellulases is sent to a contactor and contacted with new lignocellulosic substrate, whereby the retained cellulases are adsorbed, and
(ii) feeding the new substrate impregnated with adsorbed cellulases into said first reactor.

3. The method of claim 2, wherein the new substrate impregnated with cellulases from the contactor is separated from the third hydrolyzate (first sweet juice).

4. The method of claim 1, wherein the sweet juice production stage is carried out in batch mode, comprising
(i) completely emptying the first and second reactors, during which a reaction mixture contained in said first reactor is sent to a filter medium, wherein a solid residue is separated from a liquid in the reaction mixture, and
(ii) sending the liquid to a separation means, at the outlet of which a liquid fourth hydrolyzate fraction comprising a second sweet juice is obtained.

5. The method of claim 4, wherein said liquid fourth hydrolyzate fraction is totally or partly introduced into said first reactor during a subsequent lignocellulose conversion stage by reintroducing fresh cellulases and new substrate.

6. The method of claim 4, wherein said liquid fourth hydrolyzate fraction is sent to the contactor to impregnate new substrate with cellulases.

7. The method of claim 6, wherein the new substrate impregnated with cellulases from the contactor is separated from the cellulase-free fourth hydrolyzate (second sweet juice).

8. The method of claim 4, wherein all of said liquid fourth hydrolyzate (second sweet juice) is sent to said second reactor.

9. The method of claim 4, further wherein
(iii) during the emptying of the second reactor, said second hydrolyzate stream from said second reactor, to which the retained cellulases from the separation means in step (a)(2) are added, is sent to a contactor, wherein said second hydrolyzate is contacted with new lignocellulosic substrate, whereby residual cellulases are adsorbed, and
(iv) feeding the new substrate impregnated with adsorbed cellulases into said first reactor.

10. The method of claim 9, further wherein
(v) said second and/or fourth hydrolyzates are separated from the new substrate impregnated with adsorbed cellulases in the contactor and the third hydrolyzate (first sweet juice) and/or the cellulase-free fourth hydrolyzate (second sweet juice) are produced.

11. The method of claim 4, wherein the fourth hydrolyzate contains <1 g/l soluble glucose oligomers.

12. The method of claim 1, wherein said separation means is an ultrafiltration membrane.

13. The method of claim 1, wherein the temperature and/or pH operating conditions of said first and second reactors are different.

14. A method of producing a lignocellulosic hydrolyzate (sweet juice) for alcoholic fermentation from a lignocellulosic substrate by enzymatic hydrolysis, comprising:
(a) a lignocellulose conversion stage, comprising
(1) contacting the lignocellulosic substrate with a cellulase solution in a first reactor to produce a first hydrolyzate, wherein said lignocellosic substrate has been pretreated to improve the susceptibility of the substrate to enzymatic hydrolysis;
(2) sending the thus-produced first hydrolyzate obtained at the outlet of said first reactor to a separation means, whereby the cellulases in the first hydrolyzate are extracted from the first hydrolyzate and retained by the separation means for return to the first reactor, to produce a cellulase-free first hydrolyzate;
(3) sending the cellulase-free first hydrolyzate to a second reactor comprising immobilized β-glucosidases, wherein said second reactor is separate from said first lignocellulose enzymatic hydrolysis reactor, to produce a second hydrolyzate, and separating the second hydrolyzate from the immobilized β-glucosidases;
(4) repeating steps (1)-(3) until the second hydrolyzate contains 1 g/l soluble glucose oligomers;
(b) a sweet juice production stage, comprising
(1) adding the retained cellulases from the separation means in step (a)(2) to the second hydrolyzate;
(2) contacting at least a portion of said second hydrolyzate including retained cellulases with new lignocellulosic substrate, whereby the retained cellulases in said portion of the second hydrolyzate are adsorbed by the new substrate and a third hydrolyzate (first sweet juice) for alcoholic fermentation is produced,
(3) recycling any remaining portion of said second hydrolyzate and the cellulases to said first reactor; and
(c) a reactor emptying stage, comprising completely emptying of the first and second reactors.

15. The method of claim 14, wherein said separation means is an ultrafiltration membrane.

16. The method of claim 14, wherein the sweet juice production stage is carried out in continuous mode, comprising
(i) separating said second hydrolyzate into at least two streams, streams H2a and H2b,
(ii) continuously feeding stream H2a into a contactor and
(iii) recycling stream H2b into said first reactor.

17. The method of claim 16, wherein stream H2a is contacted with new lignocellulosic substrate in the contactor, whereby cellulases in H2a are adsorbed on and thereby impregnated on the substrate, and the third hydrolyzate (first sweet juice) is produced.

18. The method of claim 17, wherein the new substrate impregnated with cellulases from the contactor is separated from the third hydrolyzate (first sweet juice) prior to being sent to said first reactor.

19. The method of claim 14, wherein the temperature and/or pH operating conditions of said first and second reactors and are different.

* * * * *